United States Patent [19]

Youngdale

[11] 3,974,195
[45] Aug. 10, 1976

[54] 2a,2b-DIHOMO-15-ALKYL-PGF$_{2\alpha}$ ANALOGS

[75] Inventor: Gilbert A. Youngdale, Portage, Mich.

[73] Assignee: The Upjohn Company, Kalamazoo, Mich.

[22] Filed: Oct. 2, 1974

[21] Appl. No.: 511,220

[52] U.S. Cl. .................. 260/410.9 R; 260/247.2 R; 260/268 R; 260/293.6 S; 260/326.2; 260/404; 260/404 S; 260/413; 260/468 D; 260/514 D; 424/305; 424/318
[51] Int. Cl.$^2$.................. C07C 61/38; C07C 69/74
[58] Field of Search......... 260/410.9 K, 413, 468 D, 260/514 D, 514 CA

[56] References Cited
UNITED STATES PATENTS 3,514,383   5/1970   Beal et al............................ 204/158

OTHER PUBLICATIONS

Karim, The Prostaglandins, pp. 313–315 (1972).

Primary Examiner—Robert Gerstl
Attorney, Agent, or Firm—Robert A. Armitage

[57] ABSTRACT 2a,2b-Dihomo-15-methyl and 15-ethyl PGF- and PGE-type compounds are disclosed with processes for making them. These compounds are useful for a variety of pharmacological purposes, including anti-ulcer, inhibition of platelet aggregation, increase of nasal patency, labor inducement at term, and wound healing.

7 Claims, No Drawings

2A,2B-DIHOMO-15-ALKYL-PGF₂ ANALOGS

BACKGROUND OF THE INVENTION

This invention relates to novel compositions of matter, to novel methods for producing them, and to novel chemical intermediates useful in those processes. Particularly, this invention relates to certain novel analogs of prostaglandins $E_1$, $F_{1\alpha}$, $F_{1\beta}$, $E_2$, $F_{2\alpha}$, and $F_{2\beta}$ in which the carboxy-terminated chain contains an additional ethylene group and the hydrogen attached to the C-15 in the prostanoic acid structure is replaced by a methyl or an ethyl group.

The known prostaglandins include, for example, prostaglandin $E_1$ (PGE₁), prostaglandin $F_1$ alpha and beta (PGF$_{1\alpha}$ and PGF$_{1\beta}$), prostaglandin $E_2$ (PGE₂), and prostaglandin $F_2$ alpha and beta (PGF$_{2\alpha}$ and PGF$_{2\beta}$). Each of the above-mentioned known prostaglandins is a derivative of prostanoic acid which has the following structure and atom numbering:

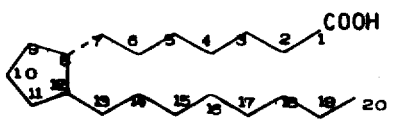

I

See, for example, Bergstrom et al., Pharmacol. Rev. 20, 1 (1968), and references cited therein. A systematic name for prostanoic acid is 7-[(2β-octyl)-cyclopent-1α-yl]-heptanoic acid.

PGE₁ has the following structure:

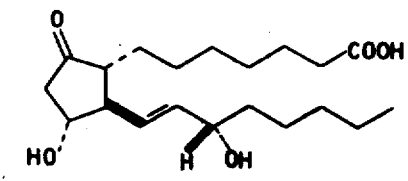

II

PGF₁ α has the following structure:

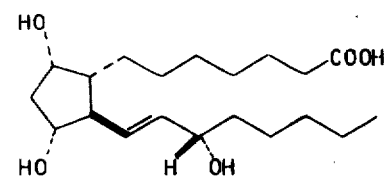

III

PGF₁ β has the following structure:

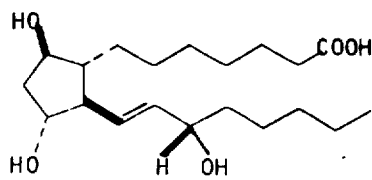

IV

PGE₂ has the following structure:

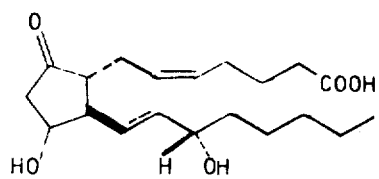

V

PGF₂ α has the following structure:

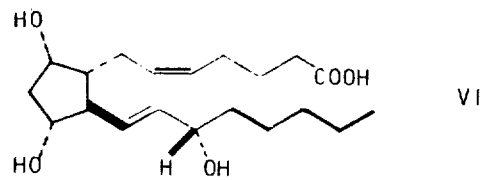

VI

PGF₂ β has the following structure:

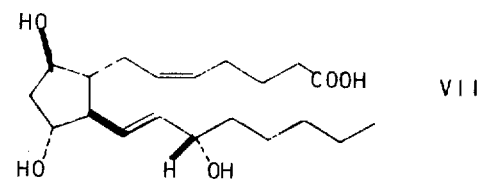

VII

In formulas II to VII, as well as in the formulas given hereinafter, broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring.

The side-chain hydroxy at C–15 in formulas II to VII is in S configuration. See Nature, 212, 38 (1966) for discussion of the stereochemistry of the prostaglandins.

The expressions "C–15" and the like identify the carbon atom in the prostaglandin or prostaglandin analog which is in the position corresponding to the position of the carbon atom of the same number in prostanoic acid (See formula I).

Molecules of the known prostaglandins each have several centers of asymmetry, and can exist in racemic (optically inactive) form and in either of the two enantiomeric (optically active) forms, i.e. the dextrorotatory and levorotatory forms. As drawn, formulas II and VII each represent the particular optically active form of the prostaglandin which is obtained from certain mammalian tissues, for example, sheep vesicular glands, swine lung, or human seminal plasma, or by carbonyl and/or double bond reduction of that prostaglandin. See, for example, Bergstrom et al., cited above. The mirror image of each of formulas II to VII represents the other enantiomer of that prostaglandin. For convenience hereinafter, use of the terms, PGE₁, PGF$_{1\alpha}$, PGF$_{1\beta}$, and the like, will mean the optically active form of that prostaglandin with the same absolute configuration as PGE₁ obtained from mammalian tissues.

PGE₁, PGE₂, and the corresponding PGF α, and PGF β compounds, and their esters, and pharmacologically acceptable salts, are extremely potent in causing various biological responses. For that reason, these compounds are useful for pharmacological purposes. See, for example, Bergstrom et al., Pharmacol. Rev. 20, 1 (1968), and references cited therein. A few of those biological responses are; antilipolytic activity as shown by antagonism of epinephrine-induced mobilization of free fatty acids or inhibition of the spontaneous release of glycerol from isolated rat fat pads; inhibition of gastric secretion in the case of the PGE compounds as shown in dogs with secretion stimulated by food or histamine infusion; activity on the central nervous system; controlling spasm and facilitating breathing in asthmatic conditions; decreasing blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen and in the case of the PGE compounds, stimulation of epidermal proliferation and keratinization as shown when applied in culture to embryonic chick and rat skin segments.

Because of these biological responses, these known prostaglandins are useful to study, prevent, control, or alleviate wide variety of diseases and undesirable physiological conditions in birds and mammals, including humans, useful domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 $\mu$g. to about 10 mg. per ml. of a pharmacologically suitable liquid vehicle or as an aerosol spray, both for topical application. The exact dose depends upon the age, weight, and condition of the patient, and on the frequency and route of administration.

The PGE, PGF$_\alpha$, and PGF$_\beta$ compounds are useful in the treatment of asthma. For example, these compounds are useful as bronchodilators or as inhibitors of mediators, such as SRS-A and histamine, which are released from cells activated by an antigen-antibody complex. Thus these compounds control spasm and facilitate breathing in conditions such as bronchial asthma, bronchitis, bronchiectasis, pneumonia, and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone). Regarding use of these compounds see South African Pat. No. 681,055.

The PGE compounds are useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 $\mu$g. to about 500 $\mu$g. per kg. of body weight per minute, or in a total daily dose by injection of infusion in the range about 0.1 to about 20 mg. per kg. of body weight per day, the exact dose depending on the age, weight, and condition of the patient or animal, and on the frequency and route of administration.

The PGE, PGF$_\alpha$, and PGF$_\beta$ compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intraveneous route of administration is preferred. Doses in the range about 0.005 to about 20 mg. per kg. of body weight per day are used, the exact dose depending on the age, weight, and condition of the patient or animal, and on the frequency and route of administration.

The PGE, PGF$_\alpha$, and PGF$_\beta$ compounds are especially useful as additives to blood, blood products, blood substitutes, and other fluids which are used in artificial extracorporeal circulation and perfusion of isolated body portions, e.g., limbs and organs, whether attached to the original body, detached and being preserved or prepared for transplant, or attachment to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

The PGE, PGF$_\alpha$, and PGF$_\beta$ compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 $\mu$g. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

The PGE, PGF$_\alpha$, and PGF$_\beta$ compounds are useful for controlling the reproductive cycle in ovulating female mammals, including humans and animals such as monkeys, rats, rabbits, dogs, cattle, and the like. By the term ovulating female mammals is meant animals which are mature enough to ovulate but not so old that regular ovulation has ceased. For that purpose, PGF$_{2\alpha}$, for example, is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the normal mammalian gestation period, especially the first and second trimesters.

The PGE and PGF compounds are useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by PGE and PGF compounds is useful in assisting sperm movement to the uterus. Cervical dilation by prostaglandins is also useful in operative gynecology such as D and C (Cervical Dilation and Uterine Curettage) where mechanical dilation may cause perforation of the uterus, cervical tears, or infections. It is also useful in diagnostic procedures where dilation is necessary for tissue examination. For these purposes, the PGE and PGF compounds are administered locally or systemically. $PGE_2$, for example, is administered orally or vaginally at doses of about 5 to 50 mg. per treatment of an adult female human, with from one to five treatments per 24 hour period. $PGE_2$ is also administered intramuscularly or subcutaneously at doses of about one to 25 mg. per treatment. The exact dosages for these purposes depend on the age, weight, and condition of the patient or animal.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptomatic alleviation, and cure of diseases involving abnormal lipid mobilization and high free fatty acid levels, e.g., diabetes mellitus, vascular diseases, and hyperthyroidism.

The PGE compounds promote and accelerate the growth of epidermal cells and keratin in animals, including humans, useful domestic animals, pets, zoological specimens, and laboratory animals. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the cite where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection of infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 2000 $\mu g./ml.$ of the PGE compound. Especially for topical use, these prostaglandins are useful in combination with antibiotics, for example, gentamycin, neomycin, polymyxin B, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.)

The $PGF_\alpha$, $PGF_\beta$, and PGE compounds, are also usful in reducing the undesirable gastrointestinal effects resulting from systemic administration of anti-inflammatory prostaglandin synthetase inhibitors, and are used for that purpose by concomitant administration of the prostaglandin and the anti-inflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins of the E and A series, including $PGE_1$ and $PGE_2$. Prostaglandin compounds are useful, for example, in reducing the undesirable gastrointestinal effects resulting from systemic administration of indomethacin, phenylbutazone, and aspirin. These are substances specifically mentioned in Partridge et al. as non-steroidal anti-inflammatory agents. But these are also known to be prostaglandin synthetase inhibitors.

The anti-inflammatory synthetase inhibitor, for example, indomethacin, aspirin, or phenylbutazone is administered in any of the ways known in the art to alleviate an inflammatory condition, for example, in any dosage regimen and by any of the known routes of systemic administration.

The prostaglandin is administered along with the anti-inflammatory prostaglandin synthetase inhibitor either by the same route of administration or by a different route. For example, if the anti-inflammatory substance is being administered orally, the prostaglandin is also administered orally or, alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin is also administered rectally or, alternatively, orally or, in the case of women, vaginally. It is especially convenient when the administration route is to be the same for both anti-inflammatory substance and prostaglandin, to combine both into a single dosage form.

The dosage regimen for the prostaglandin in accord with this treatment will depend upon a variety of factors, including the type, age, weight, sex and medical condition of the mammal, the nature and dosage regimen of the anti-inflammatory synthetase inhibitor being administered to the mammal, the sensitivity of the particular individual mammal to the particular synthetase inhibitor with regard to gastrointestinal effects, and the particular prostaglandin to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the prostaglandin to reduce and then substantially to eliminate those undesirable effects.

Several related compounds have been reported in the literature. 2a,2b-Dihomo-PGE$_1$ and 2a,2b-dihomo-PGE$_2$ have been reported by Struijk, et al., Nobel Symposium 2:51 (1967).

SUMMARY OF THE INVENTION

This invention provides novel 2a,2b-dihomo-15-methyl and 15-ethyl prostaglandin E$_1$, E$_2$, F$_{1\alpha}$, F$_{2\alpha}$, F$_{1\beta}$, and F$_{2\beta}$ analogs. Further, it provides both epimeric configurations at C–15 and provides esters and pharmacologically acceptable salts of said analogs. It also provides novel processes for preparing the hereinabove described analogs, esters, and salts.

The novel prostaglandin analogs of this invention each have an ethylene group inserted between C–2 and C–3 in the carboxy terminated chain. Also at the C–15 position the novel prostaglandin analogs have either a methyl or an ethyl group in place of the hydrogen attached to C–15 in the corresponding parent prostaglandin compounds. Also both epimeric configurations at C–15 are provided. These compounds are represented by the generic formula

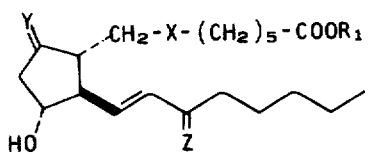

wherein X is cis —CH=CH— or —CH$_2$CH$_2$—;
wherein Y is

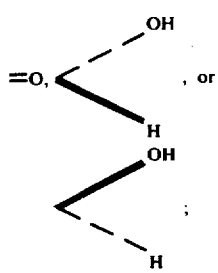

wherein Z is

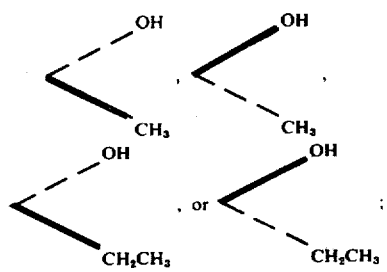

wherein R$_1$ is hydrogen, alkyl of one to 12 carbon atoms, inclusive, a pharmacologically acceptable cation,

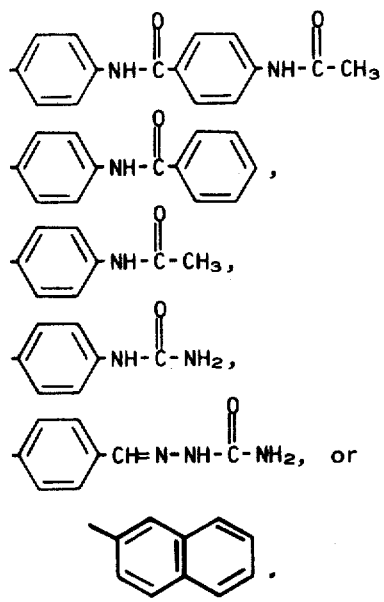

Examples of the alkyl esters of one to 12 carbon atoms included in this invention are methyl, ethyl, propyl, butyl, pentyl, hexyl, heptyl, octyl, nonyl, decyl, undecyl, dodecyl, and isomeric forms thereof.

Included in the novel compounds of this invention are the 15-epimers. Where the hydroxy group configuration at C–15 is the same as that of the natural prostaglandin PGE$_1$, identified as the "S" configuration, the name of the prostaglandin analog will include "15(S)". When the 15-epimer is intended the name of the analog will include "15(R)". When both epimeric forms ae intended the name of the prostaglandin analog will include "15(RS)". Further since the carboxy-terminated side chain of the novel compounds of this invention have an ethylene group inserted between C–2 and C–3, the names of the novel compounds of this invention include "2a,2b-dihomo".

The numerical designation of the skeletal carbon atoms is unchanged, except that between C–2 and C–3 will be carbon atoms C–2a and C–2b. Also since a methyl or ethyl group replaces the hydrogen at C–15, the name of the novel compounds of this invention include "15-methyl" or "15-ethyl" respectively.

For example, 2a,2b-dihomo-15(S)-15-methyl-PGE$_1$ one of the novel compounds of this invention, is represented by:

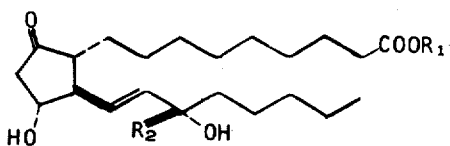

VIII when R$_1$ is hydrogen and R$_2$ is methyl. 2a,2b-Dihomo-15(S)-15-ethyl-PGE$_1$, another novel compound of this invention, is represented by formula VIII when R$_1$ is hydrogen and R$_2$ is ethyl.

A 15-epimer of Formula VIII, 2a,2b-dihomo-15(R)-15-methyl-PGE$_1$ is also a novel compound of this invention and is represented by:

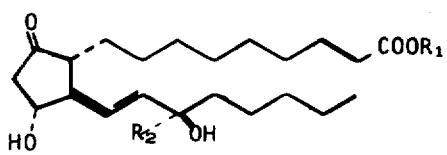

IX wherein R$_1$ is hydrogen and R$_2$ is methyl. 2a,2b-Dihomo-15(R)-15-ethyl-PGE$_1$, another novel compound of this invention, is represented by Formula IX when R$_1$ is hydrogen and R$_2$ is ethyl.

2a,2b-Dihomo-15(S)-15-methyl-PGE$_2$, another compound of this invention, is represented by:

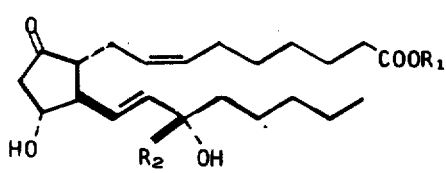

X when R$_1$ is hydrogen and R$_2$ is methyl. 2a,2b-Dihomo-15(S)-15-ethyl-PGE$_2$, another compound of this invention, is represented by formula X when R$_1$ is hydrogen and R$_2$ is ethyl.

2a,2b-Dihomo-15(R)-15-methyl-PGE$_2$, another compound of this invention, is represented by

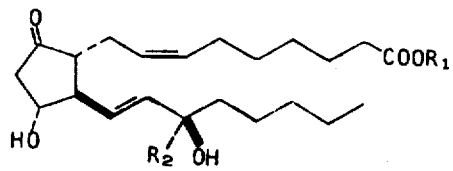

XI when R$_1$ is hydrogen and R$_2$ is methyl. 2a,2b-Dihomo-15(R)-15-ethyl-PGE$_2$, another compound of this invention is represented by formula XI when R$_1$ is hydrogen and R$_2$ is ethyl.

The F$_\alpha$ and F$_\beta$ type compounds of this invention can be similarly represented. For example, 2a,2b-dihomo-15(S)-15-methyl-PGF$_{1\alpha}$ and 2a,2b-dihomo-15(S)-15-ethyl-PGF$_{1\alpha}$ are represented by

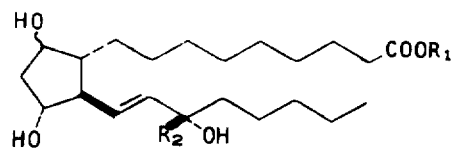

XII when ~ indicates attachment of the hydroxyl group to the cyclopentane ring in the alpha configuration, i.e., ~ is alpha, R$_1$ is hydrogen, and R$_2$ is methyl and ethyl, respectively. 2a,2b-Dihomo-15(S)-15-methyl-PGF$_{1\beta}$ and 2a,2b-dihomo-15(S)-15-ethyl-PGF$_{1\beta}$ are represented by formula XII when ~ indicates attachment of the hydroxyl group to the cyclopentane ring in the beta configuration, i.e., ~ is beta, R$_1$ is hydrogen, and R$_2$ is methyl and ethyl respectively.

Also included in the invention, for example, are the 15(R) compounds, 2a,2b-dihomo-15(R)-15-methyl-PGF$_{1\alpha}$, 2a,2b-dihomo-15(R)-15-ethyl-PGF$_{1\alpha}$, 2a,2b-dihomo-15(R)-15-methyl-PGF$_{1\beta}$, and 2a,2b-dihomo-15(R)-15-ethyl-PGF$_{1\beta}$, which can be represented by

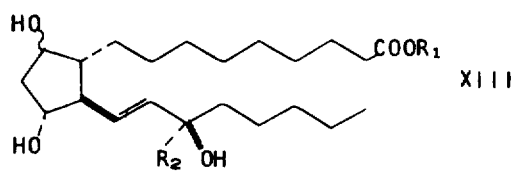

XIII when ~ indicates either alpha or beta attachment, R$_1$ is hydrogen, and R$_2$ is methyl or ethyl.

The 15(S) and 15(R) compounds of the F$_2$ series, 2a,2b-dihomo-15(S)-15-methyl-PGF$_{2\alpha}$, 2a,2b-dihomo-15(S)-15-ethyl-PGF$_{2\alpha}$, 2a,2b-dihomo-15(S)-15-methyl-PGF$_{2\beta}$, 2a,2b-dihomo-15(S)-15-ethyl-PGF$_{2\beta}$, 2a,2b-dihomo-15(R)-15-methyl-PGF$_{2\alpha}$, 2a,2b-dihomo-15(R)-15-ethyl-PGF$_{2\alpha}$, 2a,2b-dihomo-15(R)-15-methyl-PGF$_{2\beta}$, and 2a,2b-dihomo-15(R)-15-ethyl-PGF$_{2\beta}$ can be represented, for the 15(S) compounds, by

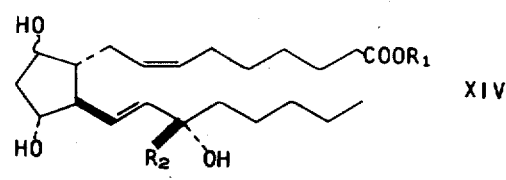

XIV when ~ is alpha or beta, R$_1$ is hydrogen, and R$_2$ is methyl or ethyl and, for the 15(R) compounds, by

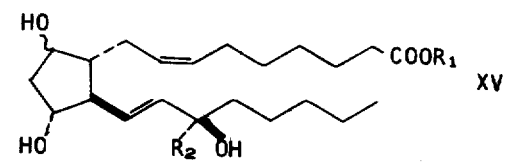

XV when ~ is alpha or beta, R$_1$ is hydrogen, and R$_2$ is methyl or ethyl.

To obtain the optimum combination of biological response, specificity, potency, and duration of activity, certain compounds within the scope of formulas VIII to XV are preferred. With reference to the definitions given above it is preferred that R$_2$, the alkyl group at C-15, be methyl, and that R$_1$ when an alkyl ester be either methyl or ethyl for optimum absorption of the compound by the experimental animal system. It is especially preferred for this purpose that R$_1$ be methyl. If a prolonged duration of activity is desired, it is especially preferred that if R$_1$ is alkyl, it be straight chained octyl, nonyl, decyl, undecyl, or dodecyl. When $R_1$ is not alkyl it is preferred that $R_1$ be hydrogen,

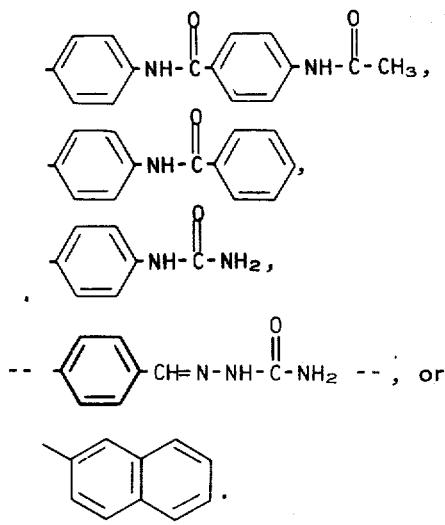

The 15(S) configuration is also preferred.

Pharmacologically acceptable salts of these formula VIII to XV compounds useful for the purposes described above are those with pharmacologically acceptable metal cations, ammonium, amine cations, or quaternary ammonium cations.

Especially preferred metal cations are those derived from the alkali metals, e.g., lithium, sodium, and potassium and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The novel formula VIII to XV compounds of this invention each cause the biological responses described above for the PGE, $PGF_\alpha$, and $PGF_\beta$ compounds, respectively, and each of these novel compounds is accordingly useful for the above-described corresponding purposes, and is used for those purposes in the same manner as described above.

The known PGE, $PGF_\alpha$, and $PGF_\beta$ compounds are all potent in causing multiple biological responses even at low doses. Moreover, for many applications, these known prostaglandins have an inconveniently short duration of biological activity. Therefore, each of these novel prostaglandin analogs is surprisingly and unexpectedly more useful than one of corresponding above-mentioned known prostaglandins for at least one of the pharmacological purposes indicated above for the latter, because it has a different and narrower spectrum of biological potency than the known prostaglandin, and therefore is more specific in its activity and causes smaller and fewer undesired side effects than when the known prostaglandin is used for the same purpose. Moreover, because of its prolonged activity, fewer and smaller doses of the novel prostaglandin analog can frequently be used to attain the desired result.

Another advantage of the novel compounds of this invention, especially the preferred compounds defined hereinabove, compared with the known prostaglandins is that these novel compounds are administered effectively orally, sublingually, intravaginally, buccally, or rectally, in addition to usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

As discussed above, the compounds of formulas VIII to XV are administered in various ways for various purposes; e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are preferred. For that purpose, it is preferred because of increased water solubility that $R_1$ in the formula VIII to XV compound be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers, are used for oral sublingual administration. For rectal or vaginal administration, suppositories prepared as known in the art are used. For tissue implants, a sterile tablet or silicone rubber capsule or other object containing or impregnated with the substance is used.

The prostaglandin analogs encompassed by formulas VIII through XV are produced by the reactions and procedures described and exemplified hereinafter.

Reference to Charts A and B herein will make clear the processes which yield the 2a,2b-dihomo-15-methyl and 15-ethyl PGF-type and PGE-type compounds of this invention.

In the Charts, $R_1$, $R_2$, and X are as hereinabove defined; $R_3$ is (1)

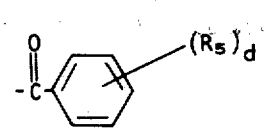

wherein $R_5$ is alkyl of one to 4 carbon atoms, inclusive, phenylalkyl of 7 to 10 carbon atoms, inclusive, or nitro, and $d$ is zero to 5, inclusive, provided that not more than two $R_5$'s are other than alkyl, and that the total number of carbon atoms in the $R_5$'s does not exceed 10 carbon atoms;

(2)

wherein $R_6$ is alkyl of one to 4 carbon atoms, inclusive;

(3)

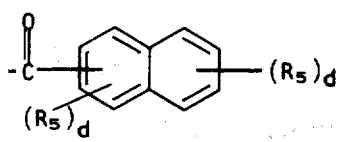

wherein $R_5$ and $d$ are as defined above and may be the same or different for each ring; or (4) acetyl. Use of acetyl or p-phenylbenzoyl is known in the art. See Corey et al., J. Am. Chem. Soc. 93, 1491 (1971).

Chart A

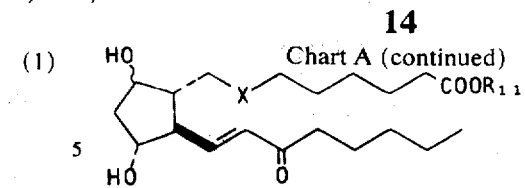 XVIII

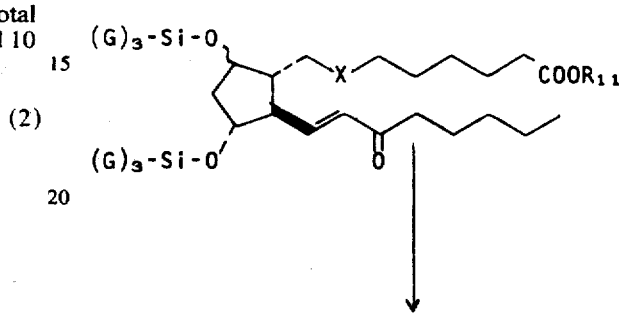 XIX

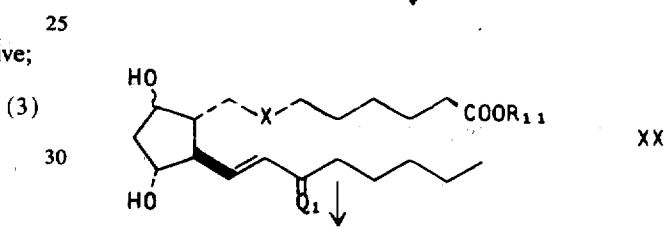 XX

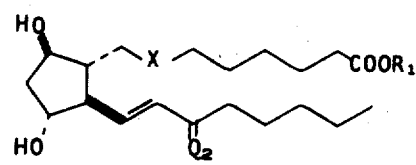 XXI

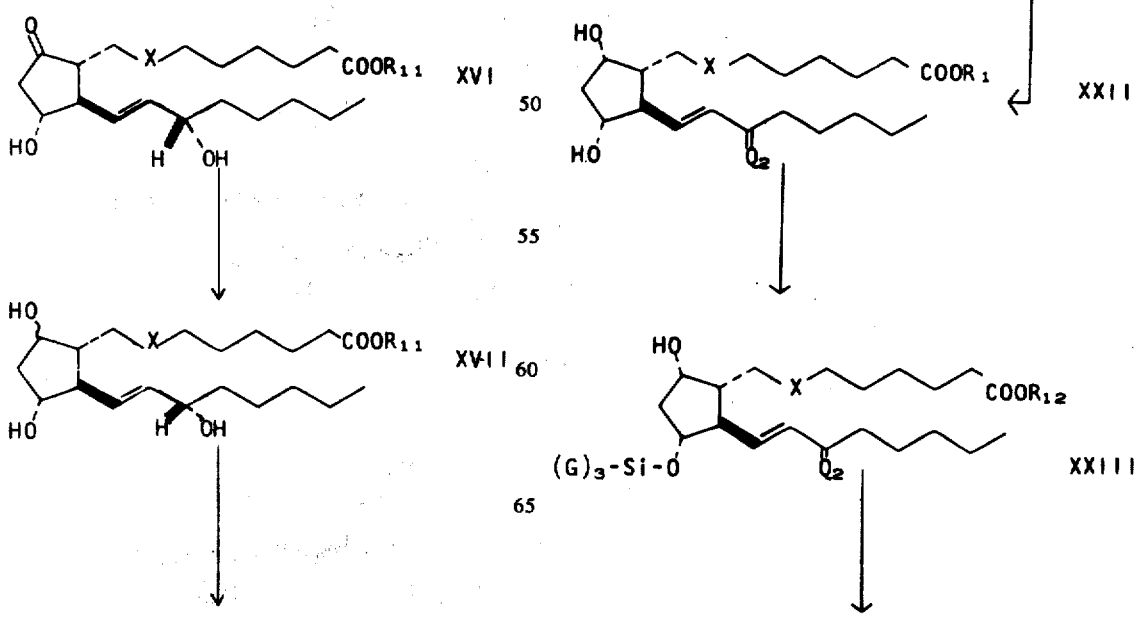

XVI

XVII

XXII

XXIII

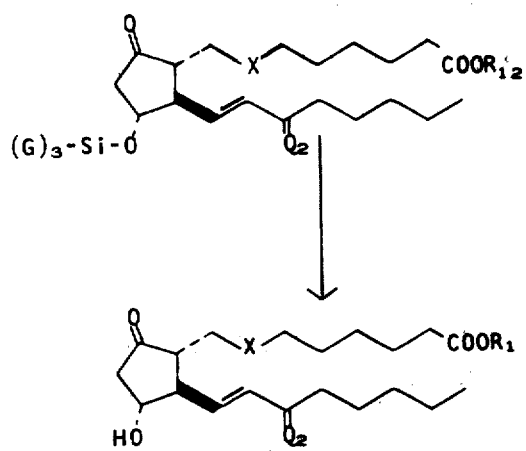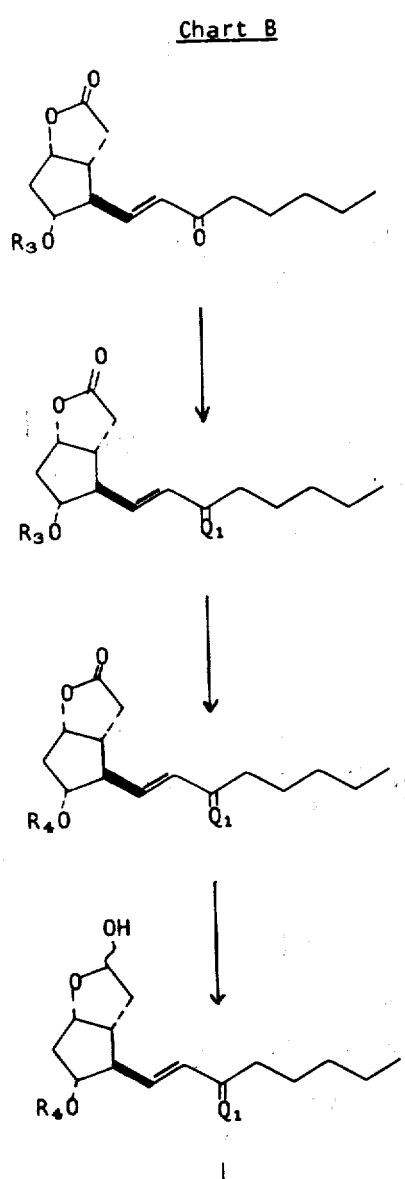

Chart B (continued)

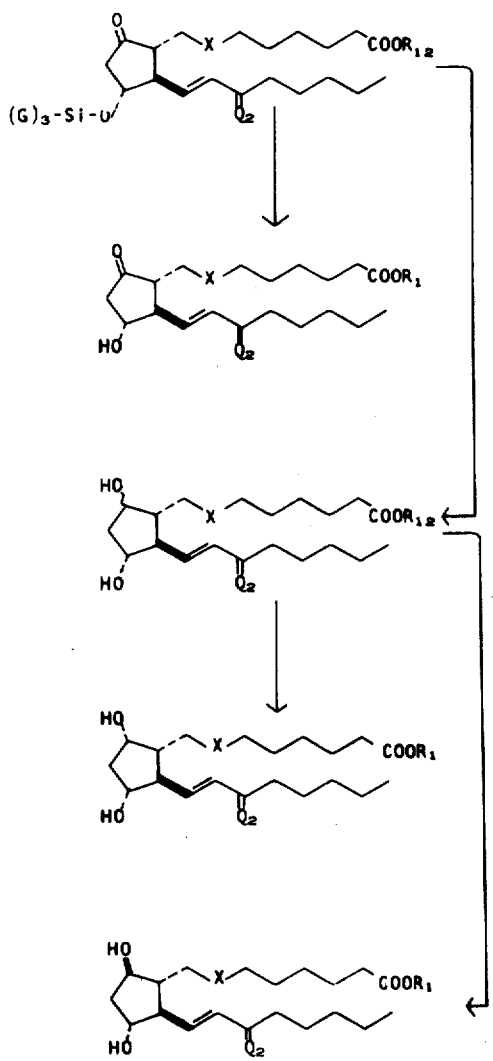

R₃ is for example, benzoyl; substituted benzoyl, e.g. (2-, 3-, or 4-)methylbenzoyl, (2-, 3-, or 4-)ethylbenzoyl, (2-, 3-, or 4-)isopropylbenzoyl, (2-, 3-, or 4-)tert-butylbenzoyl, )teret-butylbenzoyl, 2,4-dimethylbenzoyl, 3,5-dimethylbenzoyl, 2-isopropyltoluyl, 2,4,6-trimethylbenzoyl), pentamethylbenzoyl, α-phenyl-(2-, 3-, or 4-)toluyl, (2-, 3-, or 4-)phenethylbenzoyl, (2-, 3-, or 4-)nitrobenzoyl, (2,4-; 2,5-; or 3,5-)-dinitrobenzoyl, 4,5-dimethyl-2-nitrobenzoyl, 2-nitro-6-phenethylbenzoyl, 3-nitro-2-phenethylbenzoyl; mono-esterified phthaloyl, e.g.

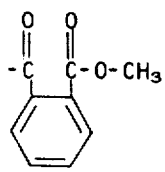

isophthaloyl, e.g.

XXXVII

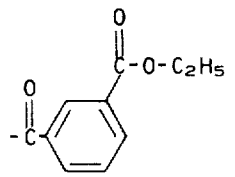

or

XXXVIII

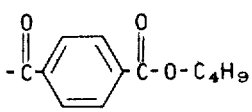

XXXIX (1- or 2-)napthoyl; and substituted naphthoyl, e.g. (2-, 3-, 4-, 5-, 6-. or 7-)methyl-1-naphthoyl, (2- or 4-)ethyl-1-naphthoyl, 2-isopropyl-1-naphthoyl; 4,5-dimethyl-1-naphthoyl, 6-isopropyl-4-methyl-1-naphthoyl, 8-benzyl-1-naphthoyl, (3-, 4-, 5-, or 8-)nitro-1-naphthoyl, 4,5-dinitro-1-naphthoyl, (3-, 4-, 6-, 7-, or 8-)methyl-1-napthoyl, 4-ethyl-2-naphthoyl and (5- or 8-)nitro-2-napthoyl.

XL Likewise R₄ is hydrogen or a "blocking group", which is defined as any group which replaces hydrogen of the hydroxy groups, which is not attacked by nor is reactive to the reagents used in the respective transformations to the extent that the hydroxy group is, and which is subsequently replaceable by hydrogen at a later stage in the preparation of the prostaglandin-like products. Several blocking groups are known in the art, e.g. tetrahydropyranyl and substituted tetrahydropyranyl (see Corey, Proceedings of the Robert A. Welch Foundation Conferences on Chemical Research XII, Organic Synthesis, pp. 51–79 (1969)). Those blocking groups which have been found useful include (a) tetrahydropyranyl; (b) tetrahydrofuranyl; (c) a group of the formula

XLI

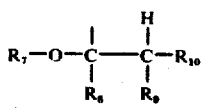

wherein $R_7$ is alkyl of one to 18 carbon atoms, inclusive, cycloalkyl or 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_8$ and $R_9$ are the same of different, being hydrogen, alkyl of one to 4 carbon atoms, inclusive, phenyl or phenyl substituted with one, 2, or 3alkyl of one to 4 carbon atoms, inclusive, or, when $R_8$ and $R_9$ are taken together, —(CH₂)$_a$— or —(CH₂)$_b$—O—(CH₂)$_c$— wherein $a$ is 3, 4, or 5, $b$ is one, 2, or 3, and $c$ is one, 2, or 3 with the proviso that $b$ plus $c$ is 2, 3, or 4, and wherein $R_{10}$ is hydrogen or phenyl; (d) a silyl group of the formula —Si(G)₃ wherein G is alkyl of one to 4 carbon atoms, inclusive, aralkyl of 7 to 12 carbon atoms, inclusive, phenyl or phenyl substituted with one or 2 fluoro, chloro, or alkyl of one to 4 carbon atoms, inclusive, and wherein the various G's of a —Si(G)₃ moiety are alike or different, or (e) a group of the formula

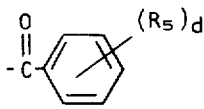

wherein $d$ and $R_5$ are defined hereinabove. $R_{11}$ is hydrogen or alkyl of one to 12 carbon atoms, inclusive. $R_{12}$ is alkyl of one to 12 carbon atoms, inclusive.

Further in these charts $Q_1$ is a mixture of

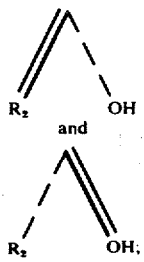

$Q_2$ is either

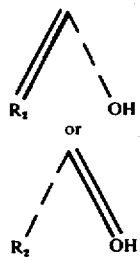

wherein $R_2$ is as defined hereinabove, and ~ indicates attachment of hydroxyl to the ring in alpha or beta configuration.

The formula-XVI acid is known in the art. See Struijk, et al., infra. The formula-XVI esters and salts can be prepared by methods hereinbelow described.

The formula-XVII compound is prepared by reduction of the formula-XVI compound by methods known in the art, followed by separation of the C-9 epimers. For example, diisobutylaluminum hydride may be used as a reducing agent, preferably at temperatures between −70° C. and −80° C. in a tetrahydrofuran solvent, followed by a chromatographic separation on silica gel.

The formula-XVIII compound is then prepared by oxidation of a secondary hydroxy group at C-15 by procedures known in the art from the formula-XVII compound. Oxidation reagents such as 2,3-dichloro-5,6-dicyano-1,4-benzoquinone (DDQ), activated manganese dioxide, or nickel peroxide, may be used. See Fieser, el al., "Reagents for Organic Synthesis" page 215, 637, and 731. John Wiley and Sons New York, N.Y.

The formula-XIX compound is then produced by silylation of the formula-XVIII compound using reagents and procedures known in the art. See, for example, Pierce, "Silylation of Organic Compounds", Pierce Chemical Co., Rockford, Ill. (1968) for procedures and Post, "Silicones and Other Organic Silicone Compounds", Reinhold Publishing Company, New York, New York (1969) for examples of silylating agents.

The formula-XX compound is then produced from the formula-XIX compound first by reaction of the formula-XIX compound with a Grignard reagent of the formula $R_2MgHal$ wherein Hal is an acceptable Grignard halide, preferably bromine and $R_2$ is methyl or ethyl, under the usual conditions, followed by hydrolysis of the Grignard complex using procedures known in the art. The reaction may be carried out, for example, using diethyl ether as a reaction solvent followed by hydrolysis in a saturated ammonium chloride solution. Finally the formula-XX compound is produced by hydrolysis of the silyl groups under mild conditions. For this purpose acid in water and a water-miscible solvent such as ethanol may advantageously be used at 25° C. under an atmosphere of an inert gas, for example, nitrogen or argon. The reaction should be complete in 2 to 6 hours.

The formula-XXI or formula-XXII compound is then prepared by chromatographic separation of the C-15 epimers of the formula-XX compound. For example, column chromatographic separation may be employed using neutral silica gel. For effective separation the methyl ester of the formula-XX compound ($R_{11}$ is methyl) is preferred. The formula-XXIII compound is produced from the formula-XXII compound by transformation of the more general $R_1$ moiety into the more restrictive $R_{12}$ moiety as discussed hereinbelow, followed by selective monosilylation of the 11-hydroxy group by methods and procedures known in the art. See the silylation reference cited hereinabove, and U.S. Pat. No. 3,822,303.

The formula-XXIV compound is then produced by oxidation of the formula-XXIII compound, for example, using the Collins reagent by procedures known in the art. See for reference J. C. Collins, et al., "Tetrahedron Letters", 3363 (1968).

The formula-XXV compound is then produced by hydrolysis of the silyl group of the formula-XXIV compound followed by transformation of the $R_{12}$ moiety of the formula-XXIV compound to the more general $R_1$ moiety of the formula-XXV compound. The hydrolysis of the silyl group proceeds by the same method as hereinabove described. The transformation of the $R_{12}$ moiety to the $R_1$ moiety is effected by methods and procedures hereinbelow described.

Referring to Chart B the formula-XXVI compound is known in the art. See for reference U.S. Pat. No. 3,778,450.

The formula-XXVII compound is produced from the formula-XXVI compound by a Grignard reaction carried out under conditions which avoid decomposition of the lactone ring, followed by hydrolysis of the Grignard complex. The Grignard reagent used is of the formula $R_2MgHal$, wherein Hal is as described above and $R_2$ is methyl or ethyl. For example, diethyl ether or tetrahydrofuran is advantageously used as a diluent. This reaction is advantageously carried out at a temperature between −70° C. and −80° C. Alternatively the formula-XXVII compound may be obtained by reaction of the formula-XXVI compound, with a trialkylaluminum at about 25° C. to yield the corresponding 15-alkyl compound of this invention. For example trimethylaluminum will yield the 15-methyl compound. The reaction will, in either case, yield the 15(RS) compound of formula-XXVII.

The formula-XXVIII compound is then obtained by deacylation of formula-XXVII compound using an alkali metal carbonate, preferably potassium carbonate, or an alkali metal methoxide, preferably sodium methoxide, in methanol at about 25° C., followed by replacement of the hydrogen atom of the C-11 hydroxy group of the deacylated compound with the blocking group of the formula $R_4$ when $R_4$ is not hydrogen or the same as $R_3$. When the blocking group is tetrahydropyranyl or tetrahydrofuranyl, the appropriate reagent, e.g. 2,3-dihydropyran or 2,3-dihydrofuran, is used in an inert solvent such as dichloromethane in the presence of an acid condensing agent such as p-toluenesulfonic acid or pyridine hydrochloride. The reagent is used in slight excess preferably at 1.0 to 1.2 times the stoichiometric amount. The reaction is carried out at about 20° to 50° C. When the blocking group is of the formula Si-(G)$_3$, silylation procedures known in the art are used. See, for example, the references cited hereinabove.

When the blocking group is of the formula

wherein $R_5$ and d are as defined above, procedures known in the art are used such as are cited in the above reference U.S. Pat. No. 3,778,450, for the acylation of compounds. Where the blocking group is the formula

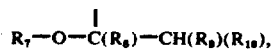

wherein $R_7$, $R_8$, $R_9$, and $R_{10}$ are as defined above, the appropriate reagent is a vinyl ether e.g. isobutyl vinyl ether or any vinyl ether of the formula $R_7$—O—C($R_8$)=C($R_9$)—($R_{10}$) wherein $R_7$, $R_8$, $R_9$, and $R_{10}$ are defined above; or an unsaturated cyclic or heterocyclic compound, e.g. 1-cyclohex-1-enyl methyl ether

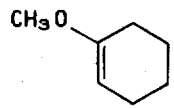

or 5,6-dihydro-4-methoxy-2H-pyran

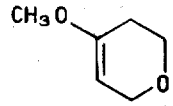

See C. B. Reese et al., Journal of American Chemical Society 89,3366 (1967). The reaction conditions for such vinyl ethers and unsaturates are similar to those for dihydropyran above. When the blocking group of the formula-XXVIII compound is identical to the protecting group of the formula-XXVII compound then the removal and replacement of the blocking group is of course eliminated.

The formula-XXIX lactol is obtained on reduction of the formula-XXVIII lactone without reducing the ethylenic group. For this purpose, diisobutyl aluminum hydride is used as known in the art. The reduction is preferably done at 31 70° to −80° C.

The formula-XXX compound is obtained by a Wittig alkylation of the lactol, the formula-XXIX compound, using the methods known in the art. When $R_{11}$ is hydrogen the phosphonium salt used in the Wittig reaction is a (6-carboxyhexyl)triphenylphosphonium halide, preferably bromide. When $R_{11}$ is an alkyl ester the corresponding [6-(alkoxycarbonyl)hexyl]triphenylphosphonium halide, preferably bromide, is used. For optimum yield it is preferred that the Wittig reaction be preformed so as to yield the free acid. Thus, by this preferred route the (6-carboxyhexyl)triphenyl phosphonium halide is used. Any $R_{11}$ ester of the formula-XXX compound is then prepared from the free acid product of the Wittig alkylation by methods and procedures hereinbelow described.

The formula-XXXI compound is then prepared by chromatographic separation of the 15-epimeric mixture of the formula-XXX compound. Chromatographic methods as known in the art such as the use of neutral silica gel chromatography may be used advantageously.

The formula-XXXII compound is then produced from the formula-XXXI compound by transformation of the $R_{11}$ moiety to the more general $R_1$ moiety by using methods and procedures hereinbelow described.

The formula-XXXIII compound is then prepared from the formula-XXXI compound by reduction of the 5,6-cis double bond of the formula-XXXI compound by metal catalytic reduction procedures known in the art. For example, using one atmosphere of hydrogen and palladium on charcoal at −15° C. in ethyl acetate the formula-XXXI compound is reduced to form the formula-XXXIII compound. See for reference B. Samuelsson, Journal of Biological Chemistry, 239, 491 (1964). The transformation of the formula-XXXIII compound to the more general formula-XXXIV compound is effected by methods and procedures hereinbelow described.

The formula-XXXV compound is produced by the methods hereinabove described. The formula-XXXVI compound is then produced by selective monosilylation of the formula-XXXV compound by the methods and procedures known in the art hereinabove described.

The formula-XXXVII compound is then produced by oxidation of the formula-XXXVI compound by methods and procedures known in the art. The oxidation is preferably effected using the Collins reagent according to the procedure hereinabove described. The formula-XXXVIII compound is the produced from the formula-XXVII compound by hydrolysis of the silyl groups as hereinabove described and transformation of the $R_{12}$ moiety to the more general $R_1$ moiety by methods and procedures hereinbelow described.

The formula-XXXIX compound is then produced from the formula-XXXVII compound by hydrolysis of the silyl group of the formula-XXVII compound by the methods and procedures hereinabove described followed by reduction of the 9-oxo group compound to a 9-hydroxy group using the methods and procedures used hereinabove described, e.g., the use of diisobutylaluminum hydride as the reducing agent.

The formula-XL PGF$_\alpha$- and formula-XLI PGF$_\beta$-type products are then produced from the formula- XXXIX compound by separation methods known in the art. For example, column chromatography with neutral silica gel may be advantageously employed. Finally, the formula-XL and XLI compounds are prepared by transformation of the $R_2$ moiety of the formula-XXXIX compound to the more general $R_1$ moiety of the formula-XL and formula-XLI compounds by methods hereinbelow described.

As discussed above, the processes herein described lead variously to acids ($R_1$ is hydrogen) or to esters.

When the alkyl ester has been obtained and an acid is desired, saponification procedures, as known in the art for F-type prostaglandins may be used.

For alkyl esters of E-type prostaglandins enzymatic processes for transformation of esters to their acid forms may be used by methods known in the art. See for reference E. G. Daniels, Producing an Esterase, U.S. Pat. No. 3,761,356.

When an acid has been prepared and an alkyl ester is desired, esterification is advantageously accomplished by interaction of the acid with the appropriate diazohydrocarbon. For example, when diazomethane is used, the methyl esters are produced. Similar use of diazoethane, diazobutane, 1-diazo-2-ethylhexane, and diazodecane, for example, gives the ethyl, butyl, 2-ethylhexyl and decyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley and Sons, Inc., New York, N.Y., Vol. 8, pp. 389–394 (1954).

An alternative method for esterification of the carboxy moiety of the acid compounds comprises transformation of the free acid to the corresponding silver salt, followed by interaction of that salt with an alkyl iodide. Examples of suitable iodides are methyl iodide, ethyl iodide, butyl iodide, isobutyl iodide, tert-butyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

Various methods are available for preparing the following esters of this invention:

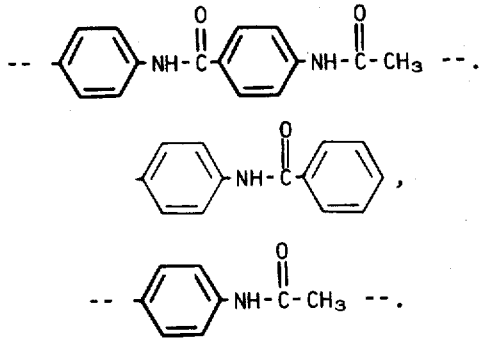

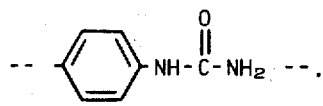

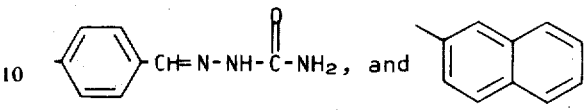

from corresponding phenols or naphthol and the free acid PG compounds differing as to yield and purity of product.

Thus by one method, the PG compound is converted to a tertiary amine salt, reacted with pivaloyl halide to give the mixed acid anhydride and then reacted with the phenol. Alternatively, instead of pivaloyl halide, an alkyl or phenysulfonyl halide is used, such as p-toluenesulfonyl chloride. See for example Belgian patents 775,106 and 776,294, Derwent Farmdoc Nos. 33705T and 39011T.

Still another method is by the use of the coupling reagent, dicyclohexylcarbodiimide. See Fieser et al., "Reagents for Organic Synthesis", pp. 231–236, John Wiley and Sons, Inc., New York (1967). The PG compound is contacted with one to ten molar equivalents of the phenol in the presence of 2–10 molar equivalents of dicyclohexylcarbodiimide in pyridine as a solvent.

The preferred novel process for the preparation of these esters, however, comprises the steps (1) forming a mixed anhydride with the PG compound and isobutylchloroformate in the presence of a tertiary amine and (2) reacting the anhydride with an appropriate phenol or naphthol.

The mixed anhydride is represented by the formula:

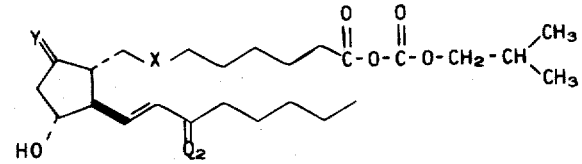

for the optically active PG compounds, wherein $Q_2$, X, and Y have the same definition as above.

The anhydride is formed readily at temperatures in the range −40° to +60° C., preferably at −10° to +10° C. so that the rate is reasonably fast and yet side reactions are minimized. The isobutylchloroformate reagent is preferably used in excess, for example 1.2 molar equivalents up to 4.0 per mole of the PG compound. The reaction is preferably done in a solvent and for this purpose acetone is preferred, although other relatively non-polar solvents are used such as acetonitrile, dichloromethane, and chloroform. The reaction is run in the presence of a tertiary amine, for example triethylamine, and the co-formed amine hydrochloride usually crystallizes out, but need not be removed for the next step.

The phenol is preferably used in equivalent amounts or in excess to insure that all of the mixed anhydride is converted to ester. Excess phenol is separated from the product by methods described herein or known in the art, for example by crystallization. The tertiary amine is not only a basic catalyst for the esterification but also a convenient solvent. Other examples of tertiary amines useful for this purpose include N-methylmorpholine, triethylamine, diisopropylethylamine, and dimethylaniline. Although they may be used, 2-methyl-pyridine and quinoline result in a slow reaction. A highly hindered amine such as 2,6-dimethylpyridine is not useful because of the slowness of the reaction.

The reaction with the anhydride proceeds smoothly at room temperature (about 20° to 30° C.) and can be followed in the conventional manner with thin layer chromatography.

The reaction mixture is worked up to yield the ester following methods known in the art, and the product is purified, for example by silica gel chromatography.

Solid esters are converted to a free-flowing crystalline form on crystallization from a variety of solvents, including ethyl acetate, tetrahydrofuran, methanol, and acetone, by cooling or evaporating a saturated solution of the ester in the solvent or by adding a miscible non-solvent such as diethyl ether, hexane, or water. The crystals are then collected by conventional techniques, e.g. filtration or centrifugation, washed with a small amount of solvent, and dried under reduced pressure. They may also be dried in a current of warm nitrogen or argon, or by warming to about 75° C. Although the crystals are normally pure enough for many applications, they may be recrystallized by the same general techniques to achieve improved purity after each recrystallization.

The compounds of this invention prepared by the processes of this invention, in free acid form, are transformed to pharmacologically acceptable salts by neutralization with appropriate amounts of the corresponding inorganic or organic base, examples of which correspond to the cations and amines listed hereinabove. These transformations are carried out by a variety of procedures known in the art to be generally useful for the preparation of inorganic, i.e., metal or ammonium salts. The choice of procedure depends in part upon the solubility characteristics of the particular salt to be prepared. In the case of the inorganic salts, it is usually suitable to dissolve an acid of this invention in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanoate, gives the solid inorganic salt if that form is desired.

To produce an amine salt, an acid of this invention is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing an acid of this invention with the stoichiometric amount of the corresponding quaternary ammonium hydroxide in water solution, followed by evaporation of the water.

The acids or esters of this invention prepared by the processes of this invention are transformed to lower alkanoates by interaction of the PG-type free-hydroxy compound with a carboxyacylating agent, preferably the anhydride of a lower alkanoic acid, i.e., an alkanoic acid of two to 8 carbon atoms, inclusive. For example, use of acetic anhydride gives the corresponding acetate. Similar use of propionic anhydride, isobutyric anhydride, and hexanoic acid anhydride gives the corresponding carboxyacylates.

The carboxyacylation is advantageously carried out by mixing the hydroxy compound and the acid anhydride, preferably in the presence of a tertiary amine such as pyridine or triethylamine. A substantial excess of the anhydride is used, preferably about 10 to about 10,000 moles of anhydride per mole of the hydroxy compund reactant. The excess anhydride serves as a reaction diluent and solvent. An inert organic diluent, for example, dioxane, can also be added. It is preferred to use enough of the tertiary amine to neutralize the carboxylic acid produced by the reaction, as well as any free carboxyl groups present in the hydroxy compound reactant.

The carboxyacylation reaction is preferably carried out in the range about 0° to about 100° C. The necessary reaction time will depend on such factors as the reaction temperature, and the nature of the anhydride and tertiary amine reactants. With acetic anhydride, pyridine, and a 25° C. reaction temperature, a 12 to 24-hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxyacylate is recovered from the diethyl ether extract by evaporation. The carboxyacylate is then purified by conventional methods, advantageously by chromatography or cyrstallization.

EXAMPLES

The invention can be more fully understood by the following examples and preparations:

All temperatures are in degrees centigrade.

Infrared absorption spectra (IR) are recorded on a Perkin-Elmer Model 421 infrared spectrophotometer. Except when specified otherwise, undiluted (neat) samples are used.

Ultraviolet spectra (UV) are recorded on a Cary Model 15 spectrophotometer.

Nuclear Magnetic Resonance (NMR) spectra are recorded on a Varian A-60 spectrophotometer on deuterochloroform solutions with tetramethylsilane as an internal standard (downfield).

Mass spectra are recorded on an Atlas CH-4 mass spectrometer with a TO-4 source (ionization voltage 70 ev).

The collection of chromatographic eluate fractions starts when the eluant front reaches the bottom of the column.

"Brine", herein, refers to an aqueous saturated sodium chloride solution.

The A-IX solvent system used in thin layer chromatography (TLC) is made up from ethyl acetate-acetic acid-2,2,4-trimethylpentane-water (90:20:50:100) according to M. Hamberg and B. Samuelsson, J. Biol. Chem. 241, 257 (1966).

"Skellysolve-B" (SSB) refers to mixed isomeric hexanes. EtOAc refers to ethyl acetate.

Silica gel chromatography, as used herein, is understood to include elution, collection of fractions, and combination of those fractions shown by TLC (thin layer chromatography) to contain the desired product free of starting material and impurities.

Preparation 1

(-)-1α-Cyclopentaneacetic acid, 3α,5α-dihydroxy-2β-[(3RS)-3-hydroxy-3-methyl-trans-1-octenyl]-, γ-lactone, 3-benzoate (Formula XXVII: R₃ is

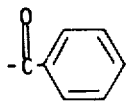

and Q₁ is a mixture of

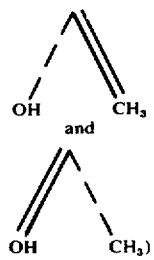

using trimethylaluminum or methyl magnesium bromide.

To a stirred solution of 1.0 g. of (-)-1α-cyclopentaneacetic acid, 3α,5α-dihydroxy-2β-(3-oxo-trans-1-octenyl)-, γ-lactone, 3-benzoate, formula XXVIX wherein R₃ is

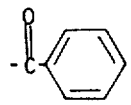

in 50 ml. of benzene at ambient temperature under nitrogen is added 0.6 ml. of trimethylaluminum giving an intense yellow color. After 15 min., the color fades significantly. TLC (50% ethyl acetate-SSB) of an aliquot quenched in etherammonium chloride shows the reaction to be complete with one main spot. The reaction is quenched by dropwise addition of 30 ml. of saturated aqueous ammonium chloride. The resulting mixture is transferred to a stoppered flask with the aid of ether and water, shaken, and filtered through a layer of Celite, washing well with ethyl acetate. The filtrate is separated and the aqueous extracted well with ethyl acetate. The organic extracts are combined, washed with brine, dried over sodium sulfate, and evaporated to give 1.1 g. of a light yellow oil. TLC (50% EtOAc-SSB) shows one main spot, Rf 0.2. TLC using other solvents including 10% acetone-methylene chloride shows main product to be one homogeneous spot. An analytical sample is prepared by chromatographing 200 mg. on 20 g. of silica gel (packed in 10% EtOAc-SSB). Taking 10-ml. fractions, elution is with 25 ml. of 10%, and 250 ml. of 50%. Fractions 8-12 contain the product-0.16 g., colorless oil, [α]_D-80° (c 1.14, chloroform). The IR shows bands at (cm⁻¹) 3500, 1770, 1715, 1600, 1580, 1490, 1450, 1315, 1270, 1175, 1110, 1070, 1045, 1025, 970, and 715. The NMR has absorptions at (CDCl₃, δ) 0.6-3.0 including singlets at 1.3 and 1.8, 4.8-5.4, 5.5-5.7, 7.2-7.6, 7.8-8.1. The mass spectrum shows ions at m/e 386, 384, 368, 315, 264, 249, 246, and 193.

Alternatively, the compound may be prepared by a Grignard reaction.

Accordingly, to a stirred solution of 0.20 g. (-)-1α-cyclopentaneacetic acid, 3α,5α-dihydroxy-2β-(3-oxo-trans-1-octenyl)-, γ-lactone, 3-benzoate, in 15 ml. of tetrahydrofuran at −78° under nitrogen is added dropwise 3 ml. of an ethereal solution 3M in methyl magnesium bromide. The solution becomes heterogeneous. After 2 hr., a TLC (50% EtOAc-SSB) of an aliquot quenched with etherammonium chloride shows the reaction to be complete. To the mixture at −78° is added dropwise 10 ml. of saturated aqueous ammonium chloride. The resulting mixture is allowed to warm with stirring to ambient temperature. The mixture is then diluted with ether and water, equilibrated, and separated. The aqueous is extracted 3 times more with ether. The organic extracts are combined, washed with brine, dried over sodium sulfate, and evaporated to give 0.21 g. of colorless oil. TLC (50% EtOAc-SSB) shows one main spot, Rf about 0.2. This material appears in every way identical to the product formed upon treatment with trimethylaluminum.

PREPARATION 2

(-)-1α-Cyclopentaneacetic acid, 3α,5α-dihydroxy-2β-[(3RS)-3-hydroxy-3-ethyl-1-trans-octenyl],γ-lactone, 3-benzoate (Formula XXVII: R₃ is

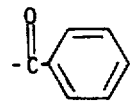

and Q₁ is a mixture of
and

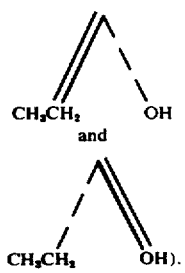

from triethylaluminum.

Following the procedure of Preparation 1, except that 0.85 ml. of triethylaluminum is substituted in place of the trimethylaluminium of Preparation 2, the compound of this preparation is produced.

PREPARATION 3

(6-Carboxyhexyl)triphenylphosphonium Bromide

A mixture of 63.6 g. of 7-bromoheptanoic acid 80 g. of triphenylphosphine, and 300 ml. of acetonitrile is refluxed for 68 hours. Then 200 ml. of acetonitrile is removed by distillation. After the remaining solution has cooled to room temperature, 300 ml. of benzene is added with stirring. After forming a crystal, the mixture is allowed to stand overnight. The solid which separates is collected by filtration giving 134.1 g. of the product as white prisms, melting point 185°–187° C. A portion is recrystallized from methanol-ether affording white prisms, melting point 185°–187°. The infrared spectrum shows absorptions at 2850, 2570, 2480, 1710, 1585, 1485, 1235, 1200, 1185, 1160, 1115, 1000, 755, 725, and 695 cm.$^{-1}$ NMR peaks are observed at 1.2–1.9, 2.1–2.6, 3.3–4.0, and 7.7–8.0 δ.

Example 1A 2a,2b-Dihomo-15(RS)-15-methyl-PGF$_2$ α , Methyl Ester (Formula XXX: wherein R$_{11}$ is methyl and Q$_1$ is a mixture of

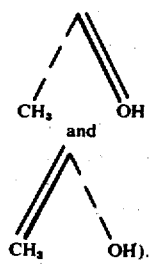

The preparation is completed by successively following the steps below.

A. (-)-1α-Cyclopentaneacetic acid, 3α,5α-dihydroxy-2β-[3(RS)-3-hydroxy-3-methyl-trans-1-octenyl]-, γ-lactone (Formula XXVIII: R$_4$ is hydrogen).

To a stirred solution of 0.50 g. of (-)-1α-cyclopentaneacetic acid, 3α,5α-dihydroxy-2β-[3(RS)-3-hydroxy-3-methyl-trans-1-octenyl]-, γ-lactone, 3-benzoate, in 10 ml. of anhydrous methanol under nitrogen at ambient temperature is added 1.0 ml. of a 25% solution of sodium methoxide in methanol. After 20 min. TLC (ethyl acetate) shows the reaction to be complete with only one vanillin-visible product. The reaction is quenched by the addition of 2 ml. of acetic acid. The solution is rotary evaporated at 40° to give an oil. The product is dissolved in ethyl acetate and extracted twice with saturated aqueous sodium bicarbonate, the aqueous extracts being combined and backwashed with ethyl acetate. The organic solutions are combined, washed with brine, dried over sodium sulfate, and evaporated to give 0.41 g. of a mobile yellow oil. Trituration twice with SSB left 0.34 g. of viscous oil. TLC (ethyl acetate) shows one main spot, Rf 0.4.

An analytical sample is prepared by chromatographing a 0.2 g. portion on 20 g. of silica gel, packed in 20% ethyl acetate-hexane. Taking 10 ml. fractions, elution is with 50 ml. of 75% ethyl acetate-hexane and 200 ml. of ethyl acetate. Fractions 8-13 contain the product as analyzed by TLC (Rf 0.4 in ethyl acetate), 0.18 g. of an oil. The mass spectrum exhibits m/e of 282, 211, 193, and 133.

B. (-)-1α-Cyclopentaneacetic Acid, 3α,5α-Dihydroxy-2β-[3(RS)-3-hydroxy-3-methyl-trans-1-octenyl]-, γ-lactone, 3-trimethylsilyl ether (Formula XXVIII: wherein R$_4$ is trimethylsilyl and Q$_1$ is a mixture of

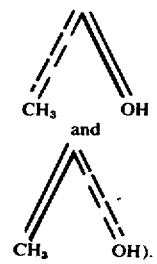

To a stirred solution of 0.50 g. of (-)-1α-cyclopentaneacetic acid, 3α,5α-dihydroxy-2β-[3(RS)-3-hydroxy-3-methyl-trans-1-octenyl]-, γ-lactone (see part A above), in 10 ml. of acetone at 0° C. under nitrogen is added 1.0 ml. (0.76 g.) of trimethylsilyldiethylamine. After 30 min., TLC (ethyl acetate) shows complete reaction. The excess reagent is quenched by dilution first with 15 ml. of diethyl ether, then addition of the resulting solution to saturated aqueous sodium bicarbonate. After equilibration, the aqueous phase is extracted 3 times with diethyl ether (3 × 20 ml.). The organic extracts are combined, washed with brine, dried over sodium sulfate, and evaporated. The watery residue is azeotroped twice with benzene under reduced pressure at 40° to give 0.60 g. of yellow oil. TLC using ethyl acetate shows one main spot, Rf 0.8 (starting material has Rf 0.4). This material is used without further purification or characterization for the procedures below.

C. (-)-1α-Cyclopentaneacetaldehyde, 3α,5α-Dihydroxy-2β-[3(RS)-3-hydroxy-3-methyl-trans-1-octenyl]-, γ-lactol, 3-trimethylsilyl ether, Formula XXIX: Q$_1$ and R$_4$ as above in this preparation.

To a stirred solution of 0.60 g. of (-)-1α-cyclopentaneacetic acid, 3α,5α-dihydroxy-2β-[3(RS)-3-hydroxy-3-methyl-trans-1-octenyl]-, γ-lactone, 3-trimethylsilyl ether (see part B above) in 10 ml. of toluene at −78° under nitrogen is added 8 ml. of 10% diisobutylaluminum hydride in toluene. Gas evolution ceases before complete addition. After addition, TLC (ethyl acetate) of an aliquot quenched in ammonium chloride shows the reaction to be complete. The reaction is quenched at −78° by the addition of 5 ml. of water and 5 ml. of tetrahydrofuran. The resulting mixture is allowed to warm to ambient temperature with stirring, transferred to a stoppered flask with the aid of ether and water, shaken, and filtered through Celite, washing well with ethyl acetate and water. The filtrate is equilibrated, and separated. The aqueous is extracted with ethyl acetate. The organic extracts are combined, washed with brine, dried over sodium sulfate, and evaporated to give, after azeotroping with benzene, 0.57 g. of yellow oil. TLC (ethyl acetate) shows one main spot Rf 0.7. The product is used without further purification or characterization for the proedures below.

D. 2a,2b-Dihomo-15(RS)-15-methyl-PGF$_2\alpha$, Methyl Ester

A mixture of 0.40 g. of 50 percent sodium hydride dispersion in mineral oil and 10 ml. of dimethylsulfoxide is stirred under nitrogen at 70°–75° for 1.5 hr. The resulting solution is allowed to cool to ambient temperature (~2 hr.). To this solution is added 2.0 g. of (6-carboxyhexyl)triphenylphosphonium bromide (preparation 3). The resulting dark red solution is stirred at ambient temperature for 1 hr. To this solution is added a solution of 0.57 g. of (-)-1α-cyclopentaneacetaldehyde, 3α,5α-dihydroxy-2β-[3(RS)-3-hydroxy-3-methyl-tans-1-octenyl], γ-lactol, 3-trimethylsilyl ether (See part C above), in 10 ml. of dimethylsulfoxide. The resulting solution is stirred overnight at ambient temperature. TLC (A-IX) of an aliquot quenched in ether-sodium bisulfate shows the reaction to be complete with one main product corresponding to the free acid, formula XXX, wherein $Q_1$ is as defined in this preparation, and $R_{11}$ is hydrogen. The reaction thereafter is quenched by addition to the mixture of 0.2M sodium bisulfate in ice water and ether. After equilibration, the aqueous phase is extracted with ether. The organic extracts are combined, washed once with dilute sodium hydroxide, twice with water then discarded. These aqueous washings are combined, then carefully acidified to pH <3 with 2M sodium bisulfate in the presence of ether. After equilibration, the aqueous phase is extracted with ether. These organic extracts are combined, washed with water, brine, dried over sodium sulfate, and evaporated to give 0.68 g. of yellow oil. The product is dissolved in ether, methylene chloride, and methanol and the resulting solution treated with excess ethereal diazomethane to give, after evaporation, 0.72 g. of an oil. This is chromatographed on 10 g. of silica gel, packed in 50 percent ethyl acetate-Skellysolve B.

EXAMPLE 1B 2a,2b-Dihomo-15(RS)-15-ethyl-PGF$_2\alpha$, Methyl Esters (Formula XXVII: $Q_1$ is a mixture of

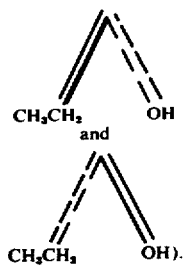

Following the procedure of Preparation 5, except using an equivalent amount of the compound of Preparation 2 in place of the compound of Preparation 1, the compound of this preparation is made.

PREPARATION 4 p-Benzamidophenol

A solution of p-hydroxyaniline (20 g.) in 200 ml. of pyridine is treated with benzoic anhydride (20 g.). After 4 hr. at about 25° C., the mixture is concentrated under reduced pressure and the residue is taken up in 200 ml. of hot methanol and reprecipitated with 300 ml. of water. The product is recrystallized from hot acetonitrile as white crystals, 8.5 g., melting point 218.0°–218.5° C.

PREPARATION 5 p-(p-Acetamidobenzamido)phenol

A solution of p-acetamidobenzoic acid (12.5 g.) in 250 ml. of tetrahydrofuran is treated with triethylamine (11.1 ml.). The mixture is then treated with isobutylchloroformate (10.4 ml.) and, after 5 min. at about 25° C., with p-aminophenol (13.3 g.) in 80 ml. of dry pyridine. After 40 min. the crude product is obtained by addition of 2 liters of water. The product is recrystalized from 500 ml. of hot methanol by dilution with 300 ml. of water as white crystals, 5.9 g., melting point 275.0°–277.0° C.

EXAMPLE 1

2a,2b-Dihomo-15(S)-15-methyl-PGF$_2\alpha$, Methyl Ester (Formula XIV: $R_1$ and $R_2$ are methyl and ~ is alpha)

2.5 g. of the oil of Example 1A is chromatographed using 400 g. of silica gel. The column is eluted with 20 percent (fractions 1 through 35) and 30 percent (fractions 36 through 55) acetone-dichloromethane and 200 ml. fractions are collected. The fractions are assayed by silica gel thin layer chromatography (acetone-dichloromethane; 2:3) Fractions 24 through 35 are combined giving 0.54 grams of a mixture of 15R and 15S isomers in oil. This oil is chromatographed using 100 g. of silica gel. The column is eluted with 20 percent acetone-dichloromethane and 100 ml. fractions are collected. The fractions 28 through 35 are combined giving 0.27 grams of 15(S) isomer as solid. The mass spectrum shows peaks at 392, 374, 343, 339, 320, and 303. The IR shows absorptions at 3380, 1735, 1455, 1435, 1375, 1260, 1200, 1170, 1125, 1100, 1080, 975, 920, and 730 cm.$^{-1}$. NMR peaks are observed at 0.9, 1.3, 0.8–2.9, 3.8, 3.9–4.5, 5.5–5.9 melting point 54°–56° C.

EXAMPLE 2

2a,2b-Dihomo-15(R)-15-methyl-PGF$_2\alpha$, Methyl Ester (Formula XV: $R_1$ and $R_2$ are methyl ~ is alpha.)

Using fractions 39 through 44 of the initial chromatographic elution of Example 1, these fractions are combined giving 0.24 g. of the 15(R) isomer as an oil. Further fractions 45 through 55 of the initial elution of Example 1 are combined giving 0.81 g. of a mixture of 15(R) and 15(S) isomers as an oil. This 0.81 g. of oil is chromatographed using 100 g. of silica gel. The column is eluted with acetone-dichloromethane (1:4) and 100 ml. fractions are collected. Fractions 19 through 22 are combined giving 0.17 g. and the 0.24 g. above are combined to form the compound of this example. The mass spectrum shows peaks at 392, 374, 361, 356, 348, 343, 339, 321, 320, and 303. The IR spectrum shows absorptions at 3380, 1735, 1655, 1455, 1435, 1365, 1320, 1265, 1200, 1170, 1145, 1120, 1100, 1080, 1060, 970, 920, and 730 cm.$^{-1}$. NMR peaks are observed at 0.8, 1.3, 0.8–2.6, 3.7, 3.9–4.4, 5.3–5.7 δ.

EXAMPLE 3

2a,2b-Dihomo-15(S)-15-ethyl-PGE$_2$$_\alpha$, Methyl Ester
(Formula XIV: R$_1$ is methyl, R$_2$ is ethyl, ~ is alpha)

Following the procedure of Example 1, except performing the chromatographic separation on the epimeric mixture of Example 1B, the compound of this example is obtained.

EXAMPLE 4

2a,2b-Dihomo-15(R)-15-ethyl-PGF$_2$$_\alpha$, Methyl Ester
(Formula XV: wherein R$_1$ is methyl R$_2$ is ethyl and ~ is alpha)

Following the procedure of Example 2, except performing the chromatographic separation on the mixture of Example 1B, the compound of this example is obtained.

EXAMPLE 5

2a,2b-Dihomo-15(S)-15-methyl-PGF$_2$$_\alpha$ (Formula XIV: R$_1$ is hydrogen, R$_2$ is methyl and ~ is alpha).

A solution of 2 g. of 2a,2b-dihomo-15(S)-15-methyl-PGF$_2$ methyl ester, the compound of Example 1, in 20 ml. of methanol is cooled to 0° C. and treated dropwise under nitrogen with 12 ml. of 10 percent aqueous sodium hydroxide solution. The mixture is then allowed to warm to room temperature and stirred for 2 hr. After removal of the methanol by evaporation at reduced pressure, the residue is diluted with water and extracted with methylene chloride. The aqueous layer is then cooled with ice, treated with 24 ml. of 2M aqueous sodium bisulfate solution and extracted immediately with ethyl acetate. The combined extracts are washed with brine, dried over anhydrous sodium sulfate and concentrated. The crude product may then be chromatographed on 150 g. of silica gel (CC-4, Mallinckrodt).

Using the procedure of Example 5, except substituting starting material as indicated below the following compounds are prepared:

Table 1

| Example | 2a,2b-Dihomo PGF$_{2\alpha}$ Compound | Starting Material (Compound of Example:) |
|---|---|---|
| 6 | 15(R)-15-methyl | 2 |
| 7 | 15(S)-15-ethyl | 3 |
| 8 | 15(R)-15-ethyl | 4 |

EXAMPLE 9

2a,2b-Dihomo-15(S)-15-methyl-PGF$_1$$_\alpha$, Methyl Ester (Formula XII: R$_1$ and R$_2$ are methyl and ~ is alpha).

A mixture of 0.50 g. of 15(S)-15-methyl-PGF$_2$$_\alpha$, methyl ester and 100 mg. of 5 percent palladium on carbon in 150 ml. of ethyl acetate is stirred at −15° C. (methanolice) under one atmosphere of hydrogen. Progress of the reaction is monitored by TLC (ethyl acetate) of aliquots using silver nitrate silica gel. After 95 min., the reaction is complete. The mixture is filtered through Celite, washing well with ethyl acetate. Rotary evaporation of the filtrate gives an oil which readily crystallized at room temperature. Recrystallization once from hexane-ethyl acetate yields the compound of this example.

The compounds of Example 10–16 are made by the procedures described in Example 9, except the starting material used differs from that of Example 9 as is indicated.

Table II

| Example | 2a,2b-Dihomo- PGF$_{1\alpha}$ Compound | Starting Material (Compound of Example:) |
|---|---|---|
| 10 | 15(R)-15-methyl, methyl ester | 2 |
| 11 | 15(S)-15-ethyl, methyl ester | 3 |
| 12 | 15(R)-15-ethyl, methyl ester | 4 |
| 13 | 15(S)-15-methyl | 5 |
| 14 | 15(R)-15-methyl | 6 |
| 15 | 15(S)-15-ethyl | 7 |
| 16 | 15(R)-15-ethyl | 8 |

EXAMPLE 17

2a,2b-Dihoma-15(R)-15-methyl PGE$_2$, Methyl Ester
(Formula XI: R$_1$ and R$_2$ are methyl).

To a stirred solution of 1.58 g. of the compound of Example 1 and 60 ml. of acetone under an atmosphere of nitrogen cooled to a −45° C. in a dry ice bath is added 6 ml. of N-trimethylsilyldiethylamine. The solution is stirred at −45° C. for one hour and then at −35° C. for one hour and then at −35° C. for one hour. Silica TLC (50 percent ethyl acetate-SSB) is used to monitor the reaction. The solution is diluted with 250 ml. of diethyl ether previously cooled to −78° C. The resulting solution is washed with 600 ml. of cold aqueous sodium bicarbonate solution. The aqueous phase is extracted with ether using four 100 ml. extractions. The combined ether extracts are washed with 100 ml. of brine and dried using sodium sulfate. Evaporation of the solvent under reduced pressure at 40° leaves an oil containing water. Benzene is added and then evaporated under reduced pressure at 40° C. leaving an oil containing water. The process is repeated unti all water is removed leaving 1.92 g. of the compound of formula XXXVI wherein X is cis-CH=CH−, R$_{11}$ is methyl, Q$_2$ is

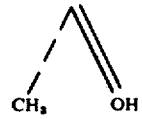

and all G's are methyl, as an oil. To a stirred solution of 100 ml. of dichloromethane and 3.96 g. of pyridine cooled in an ice bath is added 2.5 g. of chromium trioxide (CrO$_3$). The mixture is then stirred at room temperature for 4 hours, then cooled in an ice bath. Then a solution of 1.92 g. of the formula-XXXVI compound described herein in 30 ml. of dichloromethane is added to the mixture cooled in the ice bath. A deposit separates immediately. The mixture is stirred for 5 minutes while cooled in the ice bath and then for 10 minutes at room temperature. The mixture is diluted with 250 ml. of ether and washed with 600 ml. of cold 0.2 M aqueous sodium bisulfate. The aqueous phase is extracted four times with 100 ml. diethyl ether. The combined ether extracts are washed with 100 ml. saturated aqueous sodium bicarbonate solution and 50 ml. of brine and dried using sodium sulfate. The solvent is evaporated under reduced pressure at 40° C. leaving an oil containing water. Benzene is added and evaporated under reduced pressure at 40° C. leaving an oil containing water. The process is repeated until all the water is removed leaving 1.55 grams of a yellow oil. The oil is chromatographed on a column packed 250 g. of TLC grade silica gel. The column is eluted with 25 percent acetone-dichloromethane and 45 ml. fractions are collected. Fractions 45 through 62 give 0.76 g. of the compound of this example as a yellow oil. NMR shows absorption at 0.7 – 1.1, 1.1–2.8, 3.68, 3.8–4.2, 5.2–5.5, 5.5–5.8 $\delta$. The mass spectrum shows peaks 390, 372, 337, 305, 287, 269, 245, 204, 178, 133. Infrared shows absorption at 3430, 2940, 2860, 1740, 1460, 1440, 1370, 1335, 1270, 1245, 1205, 1160, 1108, and 975 cm.$^{-1}$.

Following the procedure of Example 9, the compounds of Examples 18 through 24, inclusive, are made using the corresponding starting material indicated in place of the 2a,2b-dihomo-15(R)-15-methyl-PGF$_2$ $\alpha$, methyl ester used in Example 9.

Table III

| Example | 2a,2b-Dihomo Compound | Starting Material (Compound of Example:) |
|---|---|---|
| 18 | 15(S)-15-methyl-PGE$_2$, methyl ester | 1 |
| 19 | 15(S)-15-ethyl-PGE$_2$, methyl ester | 3 |
| 20 | 15(R)-15-ethyl-PGE$_2$, methyl ester | 4 |
| 21 | 15(S)-15-methyl PGE$_1$, methyl ester | 9 |
| 22 | 15(R)-15-methyl PGE$_1$, methyl ester | 10 |
| 23 | 15(S)-15-ethyl PGE$_1$, methyl ester | 11 |
| 24 | 15(R)-15-ethyl PGE$_1$, methyl ester | 12 |

EXAMPLE 25

2a,2b-Dihomo-15(S)-15-methyl-PGE$_2$ (Formula X: R$_1$ is hydrogen and R$_2$ is methyl).

The compound of this example is prepared by enzyme hydrolysis and is described hereinbelow.

A. Enzyme Preparation

Freshly harvested colony pieces Plexaura homomalla (Esper), 1792 forma S (10 kilograms), are chopped into pieces less than 3 cm. in their longest dimension and then covered with about 3 volumes (20 l.) of acetone. The mixture is stirred at about 25° C. for about 1 hour. The solids are separated by filtration, washed with a quantity of acetone, air dried, and finally stored at about −20° C. as a coarse enzymatic powder.

B. Esterase Hydrolysis

A suspension of esterase composition from Plexaura homomalla (part A above) and 25 ml. of water is combined with a solution of 2a,2b-dihomo-15(S)-15-methyl PGE$_2$, methyl ester. In about 8 ml. of methanol the mixture is stirred at about 25° C. for 24 hours then 50 ml. of acetone is added and the mixture is stirred briefly, filtered, and the filtrate is concentrated under reduced pressure. The aqueous residue is acidified to pH 3.5 with citric acid and extracted with dichloromethane. The combined extracts are concentrated under reduced pressure to the title compound.

Following the procedure of Example 25 the compounds of Examples 26–32 are prepared from the indicated starting material.

Table IV

| Example | 2a,2b-Dihomo-Compound | Starting Material (Compound of Example:) |
|---|---|---|
| 26 | 15(R)-15-methyl-PGE$_2$ | 17 |
| 27 | 15(S)-15-ethyl-PGE$_2$ | 19 |
| 28 | 15(R)-15-ethyl-PGE$_2$ | 20 |
| 29 | 15(S)-15-methyl-PGE$_1$ | 21 |
| 30 | 15(R)-15-methyl-PGE$_1$ | 22 |
| 31 | 15(S)-15-ethyl-PGE$_1$ | 23 |
| 32 | 15(R)-15-ethyl-PGE$_1$ | 24 |

EXAMPLE 33

2a,2b-Dihomo-15(S)-15-methyl-PGF$_{2\beta}$, Methyl Ester (Formula XIV: R$_1$ and R$_2$ are methyl and ∼ is beta).

A. 2a,2b-Dihomo-15(S)-15-methyl-PGE$_2$ methyl ester is reacted with sodium borohydride in methanol at −15° C. to produce 9-hydroxy epimers.

B. The compound of this example is separated from its 9-alpha epimer by column chromatography on silica gel using the epimeric mixture of part A of this example.

Following the procedure of Example 33, the compound of Examples 34–40 are made from the indicated starting material.

Table V

| Example | 2a,2b-Dihomo-PGF$_{2\beta}$ Compounds | Starting Material (Compound of Example:) |
|---|---|---|
| 34 | 15(R)-15-methyl, methyl ester | 17 |
| 35 | 15(S)-15-ethyl, methyl ester | 19 |
| 36 | 15(R)-15-ethyl, methyl ester | 20 |
| 37 | 15(S)-15-methyl | 25 |
| 38 | 15(R)-15-methyl | 26 |
| 39 | 15(S)-15-ethyl | 27 |
| 40 | 15(R)-15-ethyl | 28 |

EXAMPLE 41

2a,2b-Dihomo-15(S)-15-methyl-PGF$_{1\beta}$, Methyl Ester (Formula XII: R$_1$ and R$_2$ are methyl and ∼ is beta).

The compound of this example is prepared by hydrogenation of the compound of Example 33 according to the procedure described in Example 9.

Examples 42–48 are prepared using the procedure of Example 41 and the indicated starting material.

Table VI

| Example | 2a,2b-Dihomo-PGF$_{1\beta}$ Compound | Starting Material (Compound of Example:) |
|---|---|---|
| 42 | 15(R)-15-methyl, methyl ester | 34 |
| 43 | 15(S)-15-ethyl, methyl ester | 35 |
| 44 | 15(R)-15-ethyl, methyl ester | 36 |
| 45 | 15(S)-15-methyl | 37 |
| 46 | 15(R)-15-methyl | 38 |
| 47 | 15(S-15-ethyl | 39 |
| 48 | 15(R)-15-ethyl | 40 |

EXAMPLE 49 p-Acetamidophenyl Ester of 2a,2b-Dihomo-15(S)-15-methyl-PGF$_2\alpha$

A solution of 2a,2b-dihomo-15(S)-15-methyl-PGF$_2\alpha$ (compound of Example 5) in acetone is treated at −10° C. with twice the stoichiometric amount of triethylamine as prostaglandin analog and also with an equal quantity of isobutylchloroformate, whereupon triethylamine hydrochloride is precipitated. After 5 minutes the mixture is treated with several fold stoichiometric excess (over the prostaglandin analog) of p-acetamidophenol in pyridine for 3 hrs. at 25° C. The solvent is removed under reduced pressure and the residue is taken up in acetonitrile and again concentrated. The crude residue is subjected to silica gel chromatography, eluting with ethyl acetate and methanol (ratio 90:10). The residue obtained by concentration of selected fractions, a solid on chilling, is the compound of this example.

Following the procedure of Example 49 using each of the PGF- and PGE-type free acids of examples above and a phenol or naphthol selected from the group consisting of p-acetamidophenol, p-(p-acetamidobenzamido)phenol, p-benzamidophenol, p-hydroxyphenylurea, p-hydroxybenzaldehyde semicarbazone, and 2-naphthol, the corresponding substituted phenyl or naphthyl esters are obtained.

I claim:

1. An optically active compound of the formula:

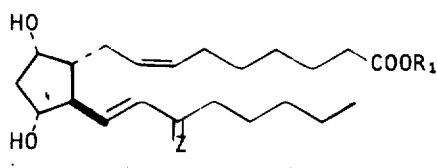

wherein Z is

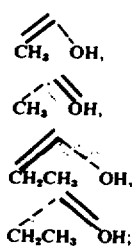

and
wherein R$_1$ is hydrogen, alkyl of one to 12 carbon atoms, inclusive,

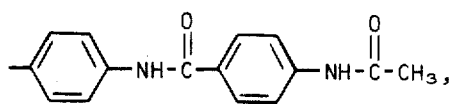

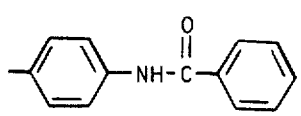

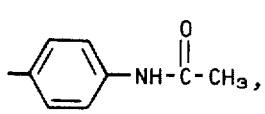

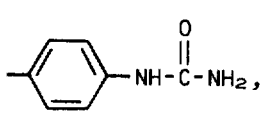

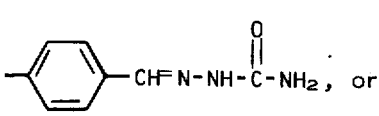

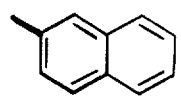

or pharmacologically acceptable salts thereof wherein R$_1$ is hydrogen.

2. A compound according to claim 1, wherein Z is

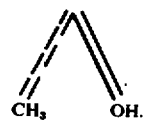

3. 2a,2b-Dihomo-15(S)-15-methyl-PGF$_{2a}$, a compound according to claim 2, wherein R$_1$ is hydrogen.

4. 2a,2b-Dihomo-15(S)-15-methyl-PGF$_{2a}$, methyl ester, a compound according to claim 2, wherein R$_1$ is methyl.

5. A compound according to claim 1, wherein Z is

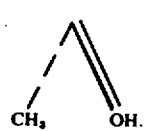

6. 2a,2b-Dihomo-15(R)-15-methyl-PGF$_{2a}$ a compound according to claim 5, wherein R$_1$ is hydrogen.

7. 2a,2b-Dihomo-15(R)-15-methyl-PGF$_{2a}$, methyl ester, a compound according to claim 5, wherein R$_1$ is methyl.

* * * * *

UNITED STATES PATENT OFFICE
CERTIFICATE OF CORRECTION

Patent No. 3,974,195      Dated August 10, 1976

Inventor(s) Gilbert A. Youngdale

It is certified that error appears in the above-identified patent and that said Letters Patent are hereby corrected as shown below:

Column 1, line 9: "$F_1\alpha_4$," should read --$F_1\alpha$--;
Column 2, line 44: "II and VII" should read -- II to VII --;
Column 5, line 67: "injection of infusion" should read -- injection or infusion --;
Column 6, line 22: "usful" should read --useful--;
Column 8, line 55: "ae" should read --are--;

Column 17, line 52: "(2-, 3-, or 4-)tert-butylbenzoyl, )teret-butylbenzoyl, 2,4-" should read -- (2-, 3, or 4-)tert-butylbenzoyl, 2,4- --; line 54: "trimethylbenzoyl)," should read -- trimethylbenzoyl, --;
Column 18, line 60: "3alkyl" should read -- 3 alkyl --;
Column 19, lines 18-21: "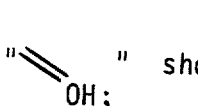" should read --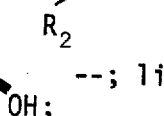--; lines 23-27: "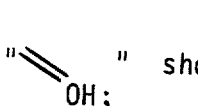" should read --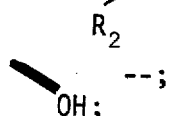--; lines 33-36: "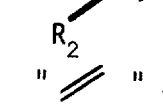" should read --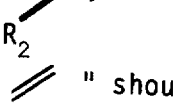--; lines 38-41: "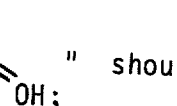" should read --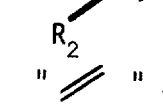--;

Column 21, line 35: "is the" should read --is of the--;
Column 22, line 5: "preferably done at 31 70° to -80° C." should read -- preferably done at -70° to -80° C. --;
Column 27, lines 24-27: "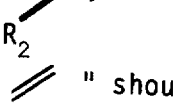" should read --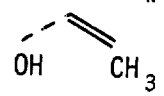--; lines 29-33: "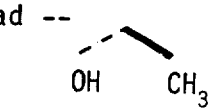" should read --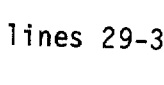--;

UNITED STATES PATENT OFFICE
CERTIFICATE OF CORRECTION

Patent No. 3,974,195   Dated August 10, 1976

Inventor(s) Gilbert A. Youngdale

It is certified that error appears in the above-identified patent and that said Letters Patent are hereby corrected as shown below:

Column 28, line 49: "and $Q_1$ is a mixture of and" should read -- and $Q_1$ is a mixture of --; lines 51-55: " 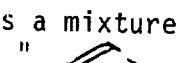 " should read -- 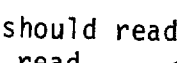 --; lines 57-61: " 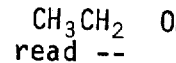 " should read -- 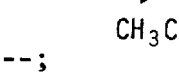 --;

Column 29, lines 28-32: "  " should read --  --; lines 33-37: " 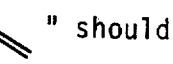 " should read --  --;

Column 30, lines 11-15: " 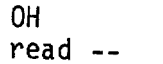 " should read -- 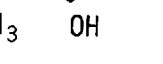 --; lines 16-20: "  " should read -- 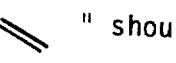 --;

Column 31, line 13: "tans" should read --trans--; lines 46-50: " 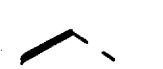 " should read -- 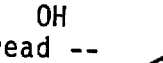 --; lines 52-56: "  " should read -- 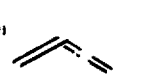 --.

Column 32, line 44: "0.8-2.9" should read -- .8-2.9 --;

Column 33, line 3: "$PGE_2\alpha$" should read --$PGF_2\alpha$--; line 25: "$PGF_2$" should read --$PGF_2\alpha$--;

UNITED STATES PATENT OFFICE
CERTIFICATE OF CORRECTION

Patent No. 3,974,195   Dated  August 10, 1976

Inventor(s) Gilbert A. Youngdale

It is certified that error appears in the above-identified patent and that said Letters Patent are hereby corrected as shown below:

Column 34, lines 49-53: "" should read --  --;

Column 37, line 12, Table VI: "15(S-15-ethyl" should read -- 15(S)-15-ethyl --; line 56: "" should read --  --;

line 59: "" should read --  --; line 62:" " should read --  --; lines 63-64: "" should read -- or  --;

Column 38, lines 42-46, claim 2: "" should read --  --;

lines 56-60, claim 5: "" should read --  -- .

Signed and Sealed this

Fourteenth Day of February 1978

[SEAL]

Attest:

RUTH C. MASON
Attesting Officer

LUTRELLE F. PARKER
Acting Commissioner of Patents and Trademarks